(12) United States Patent
Phillips

(10) Patent No.: US 10,045,973 B2
(45) Date of Patent: Aug. 14, 2018

(54) COMPOSITIONS AND METHODS FOR TREATING NOCTURNAL ACID BREAKTHROUGH AND OTHER RELATED DISORDERS

(71) Applicant: The Curators of the University of Missouri, Columbia, MO (US)

(72) Inventor: Jeffrey Owen Phillips, Ashland, MO (US)

(73) Assignee: THE CURATORS OF THE UNIVERSITY OF MISSOURI, Columbia, MO (US)

(*) Notice: Subject to any disclaimer, the term of this patent is extended or adjusted under 35 U.S.C. 154(b) by 0 days.

(21) Appl. No.: 14/996,985

(22) Filed: Jan. 15, 2016

(65) Prior Publication Data

US 2016/0367538 A1    Dec. 22, 2016

Related U.S. Application Data

(63) Continuation of application No. 12/173,493, filed on Jul. 15, 2008, now abandoned, which is a continuation of application No. 11/380,177, filed on Apr. 25, 2006, now abandoned.

(60) Provisional application No. 60/675,123, filed on Apr. 26, 2005.

(51) Int. Cl.
*A61K 31/4439* (2006.01)
*A61K 31/4745* (2006.01)

(52) U.S. Cl.
CPC ...... *A61K 31/4439* (2013.01); *A61K 31/4745* (2013.01)

(58) Field of Classification Search
CPC ..................... A61K 31/4439; A61K 31/4745
See application file for complete search history.

(56) References Cited

U.S. PATENT DOCUMENTS

2004/0248942 A1* 12/2004 Hepburn ............... A61K 47/02
514/338

OTHER PUBLICATIONS

Business Wire (http://www.businesswire.com/news/home/20041101005275/en/Santarus-Announces-Presentation-Clinical-Data-Comparing-ZEGERID, accessed Oct. 23, 2014, published Nov. 1, 2004) (Year: 2004).*

* cited by examiner

*Primary Examiner* — Angela C Brown-Pettigrew
(74) *Attorney, Agent, or Firm* — Mayer Brown LLP

(57) ABSTRACT

The present invention relates to, inter alia, pharmaceutical compositions comprising an acid labile proton pump inhibitor and a buffering agent and to use of such compositions in treating nocturnal acid breakthrough.

12 Claims, No Drawings

COMPOSITIONS AND METHODS FOR TREATING NOCTURNAL ACID BREAKTHROUGH AND OTHER RELATED DISORDERS

FIELD OF THE INVENTION

The present invention relates to, inter alia, pharmaceutical compositions comprising an acid labile proton pump inhibitor and a buffering agent; to methods for manufacture of such compositions, and to use of such compositions in treating and preventing diseases and disorders including but not limited to nocturnal acid breakthrough and nighttime heartburn.

BACKGROUND OF THE INVENTION

Gastrointestinal disorders such as active duodenal ulcers, gastric ulcers, gastroesophageal reflux disease (GERD), nocturnal acid breakthrough, severe erosive esophagitis, poorly responsive symptomatic GERD, and pathological hypersecretory conditions such as Zollinger Ellison syndrome represent a major health concern impacting millions of people globally. In fact, it is estimated that as many as 60 million Americans alone experience acid reflux at least once a month, while approximately 19 million Americans suffer from GERD.

In the past, the above-described (and other related) gastrointestinal disorders and their associated symptoms have been treated with $H_2$ histamine antagonists and antacids. Unfortunately, many such available treatments are not very effective in ameliorating the disorders themselves or their symptoms; additionally, many produce adverse side effects including, among others, constipation, diarrhea, and thrombocytopenia. Moreover, $H_2$ antagonists such as ranitidine and cimetidine are relatively costly modes of therapy generally requiring multiple daily doses to produce some control of acid secretion. In addition, tolerance to $H_2$ antagonists increases with continued use thus prohibiting clinical utility in chronic dosing settings.

More recently, at least some of the above-described gastrointestinal disorders have been treated with proton pump inhibitors (also called PPIs). PPIs are believed to reduce gastric acid production by inhibiting $H^+$, $K^+$-ATPase of the parietal cell—the final common pathway for gastric acid secretion. One particular class of PPIs includes substituted benzimidazole compounds that contain a sulfinyl group bridging substituted benzimidazole and pyridine rings.

At neutral pH, these PPIs are chemically stable, lipid-soluble compounds that have little or no inhibitory activity. It is believed that the neutral PPIs reach parietal cells from the blood and diffuse into the secretory canaliculi where they become protonated and thereby trapped. The protonated agent is then believed to rearrange to form a sulfenic acid and a sulfenamide. The sulfenamide, in turn, is thought to interact covalently with sulfhydryl groups at critical sites in the extracellular (luminal) domain of the membrane-spanning $H^+$, $K^+$-ATPase. See, Hardman et al., *Goodman & Gilman's The Pharmacological Basis of Therapeutics*, p. 907, $9^{th}$ ed. (1996).

The Assignee of the instant application, The Curators of the University of Missouri, was a party of a joint research agreement with Santarus, Inc. at the time the invention was made.

Unfortunately, most commercially available PPIs are unstable at neutral or acidic pH and undergo decomposition in gastrointestinal fluid upon oral administration, thereby resulting in loss of therapeutic activity. To overcome this acid instability, such compounds are typically formulated for oral delivery as enteric coated solid dosage forms, for example enteric coated tablets; the enteric coating protects the drug from contact with acidic stomach secretions. An undesirable consequence of such enteric coating is that therapeutic onset time is significantly delayed by comparison with non-enteric coated dosage forms. Such prolonged time to therapeutic onset is particularly undesirable for patients in need of rapid relief from one or more of the above described disorders or symptoms.

For example, U.S. Pat. No. 4,786,505 to Lovgren et al. discloses that a pharmaceutical oral solid dosage form of omeprazole must be protected from contact with acidic gastric juice by an enteric coating to maintain its pharmaceutical activity. That patent describes an enteric coated omeprazole preparation containing an alkaline core comprising omeprazole, a subcoating over the core, and an enteric coating over the subcoating.

Patients with GERD are typically given a once-daily dose of enteric coated PPI, administered in the morning, to manage daytime meal-induced gastric acid secretion. However, normal gastric acid secretion follows a circadian rhythm, with gastric acid secretion being most pronounced in the evening and early night. This results in a surge of gastric acidity around 2:00 am, with acid secretion decreasing toward the later morning. See e.g. Moore, J. G., Englert E., *Circadian rhythm of gastric acid secretion in man.* Nature 1970; 226:1261-2 and Prewett, E. J., Smith, J. T., Nwokolo, C. U., et al., *Twenty-four hour intragastric acidity and plasma gastrin concentration profiles in female and male subjects*. Clin. Sci. (Lond) 1991; 80:619-24. Unfortunately, it is recognized that commercially available enteric coated proton pump inhibitors fail to adequately control nighttime gastric acid secretion and nighttime GERD symptoms in many patients, regardless of when administered. For example, according to Tutuian R, et al., "[n]octurnal acid breakthrough occurs on any dosing regimen of oral proton pump inhibitors." Alimentary Pharmacology & Therapeutics 2002; 16(3): 473-477. Furthermore, according to Katz P O, et al., "[n]octurnal acid breakthrough is frequently seen on proton pump inhibitors twice daily and is often accompanied by oesophageal reflux. This has important implications for medical therapy in patients with severe gastro-esophageal reflux and Barrett's oesophagus." *Gastro-oesophageal reflux associated with nocturnal gastric acid breakthrough on proton pump inhibitors*. Alimentary Pharmacology & Therapeutics 1999; 12(12): 1231-1234.

Moreover, prolonged nocturnal esophageal acid exposure has been shown to contribute to the development of erosive esophagitis. See, e.g. Orr, W. C., Allen, M. L., Robinson, M. *The pattern of nocturnal and diurnal esophageal acid exposure in the pathogenesis of erosive mucosal damage* Am J Gastroenterol. 1994 April; 89(4):509-12 and Hatlebakk, J. G., Berstad, A. *Endoscopic grading of reflux oesophagitis: what observations correlate with gastroesophogeal reflux?* Scand. J. Gastroenterol. 1997; 32:760-5.

Clearly, therefore, an unmet medical need exists for new formulations of proton pump inhibitors that can treat nighttime acid breakthrough and/or nighttime heartburn and other acid related disorders.

SUMMARY OF THE INVENTION

In various embodiments, the present invention provides pharmaceutical compositions comprising at least one acid labile proton pump inhibitor and at least one buffering agent. Also provided are methods of treating and/or preventing acid related gastrointestinal disorders by administering to a subject one or more compositions of the invention. In one embodiment, methods are provided for treating and/or preventing nighttime acid breakthrough and/or nighttime heartburn and related symptoms thereof.

DETAILED DESCRIPTION OF THE INVENTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the art of pharmaceutical sciences or the art relevant to the range or element at issue. The amount of broadening from the strict numerical boundary depends upon many factors. For example, some of the factors to be considered may include the criticality of the element and/or the effect a given amount of variation will have on the performance of the claimed subject matter, as well as other considerations known to those of skill in the art. Thus, as a general matter, "about" or "approximately" broaden the numerical value. For example, in some cases, "about" or "approximately" may mean±5%, or ±10%, or ±20%, or ±30% depending on the relevant technology. Also, the disclosure of ranges is intended as a continuous range including every value between the minimum and maximum values recited as well as any ranges that can be formable thereby.

It is also to be understood that any ranges, ratios and ranges of ratios that can be formed by any of the numbers or data present herein represent further embodiments of the present invention. This includes ranges that can be formed that do or do not include a finite upper and/or lower boundary. For example, by way of illustration and not limitation, in one embodiment, a proton pump inhibitor is present in a composition of the invention in an amount of about 1 to about 3000 mg; in another embodiment, a buffering agent is present in a composition of the invention in an amount of about 200 mg to about 3500 mg. One of skill in the art will therefore recognize, for example, that additional embodiments include situations where a composition has a PPI:buffering agent weight ratio of less than or greater than 1:200, less than or greater than about 1:3500, less than or greater than 15:1 (3000/200), or less than or greater than about 0.85 (3000:3500), or in ranges of about 1:200 to about 1:3500, about 1:3500 to about 15:1, etc. Accordingly, the skilled person will appreciate that many such ratios, ranges, and ranges of ratios can be unambiguously derived from the data and numbers presented herein and all represent embodiments of the present invention.

Proton Pump Inhibitors

Compositions of the invention comprise at least one pharmaceutically acceptable acid labile PPI, for example a substituted imidazole, tetrabenzimidazole, or benzimidazole $H^+,K^+$-ATPase PPI. The term proton pump inhibitor or PPI means any acid labile pharmaceutical agent possessing pharmacological activity as an inhibitor of $H+/K+$-ATPase. A PPI may, if desired, be in the form of free base, free acid, salt, ester, hydrate, anhydrate, amide, enantiomer, isomer, tautomer, prodrug, polymorph, derivative, or the like, provided that the free base, salt, ester, hydrate, amide, enantiomer, isomer, tautomer, prodrug, or any other pharmacologically suitable derivative is therapeutically active or undergoes conversion within or outside of the body to a therapeutically active form.

In one embodiment, illustrative PPIs are those compounds of Formula (I):

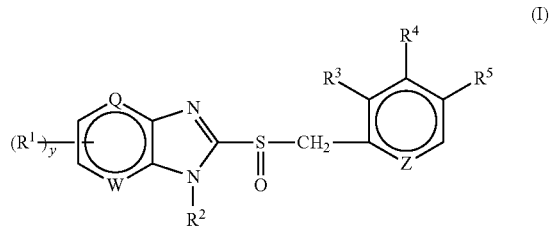

wherein
$R^1$ is hydrogen, alkyl, halogen, cyano, carboxy, carboalkoxy, carboalkoxyalkyl, carbamoyl, carbamoylalkyl, hydroxy, alkoxy which is optionally fluorinated, hydroxyalkyl, trifluoromethyl, acyl, carbamoyloxy, nitro, acyloxy, aryl, aryloxy, alkylthio, or alkylsulfinyl;
$R^2$ is hydrogen, alkyl, acyl, acyloxy, alkoxy, amino, aralkyl, carboalkoxy, carbamoyl, alkylcarbamoyl, dialkylcarbamoyl, alkylcarbonylmethyl, alkoxycarbonylmethyl, or alkylsulfonyl;
$R^3$ and $R^5$ are the same or different and each is hydrogen, alkyl, $C_{1-4}$ lower alkyl (e.g. methyl, ethyl, etc.), alkoxy, amino, or alkoxyalkoxy;
$R^4$ is hydrogen, alkyl, $C_{1-4}$ lower alkyl (e.g. methyl, ethyl, etc.), alkoxy which may optionally be fluorinated, or alkoxyalkoxy;
Q is nitrogen, CH, or $CR^1$;
W is nitrogen, CH, or $CR^1$;
y is an integer of 0 through 4; and
Z is nitrogen, CH, or $CR^1$;
or a free base, salt, ester, hydrate, amide, enantiomer, isomer, tautomer, prodrug, polymorph, or derivative thereof.

Specific examples of suitable PPIs include esomeprazole (also referred to as S-omeprazole), ilaprazole (U.S. Pat. No. 5,703,097), lansoprazole, omeprazole, pantoprazole, pariprazole, rabeprazole, tenatoprazole, leminoprazole and neparazole or a free base, a free acid, or a salt, hydrate, ester, amide, enantiomer, isomer, tautomer, polymorph, prodrug, or derivative of such compounds.

Other proton pump inhibitors include but are not limited to: soraprazan (Altana); AZD-0865 (AstraZeneca); YH-1885 (PCT Publication WO 96/05177) (SB-641257) (2-pyrimidinamine, 4-(3,4-dihydro-1-methyl-2(1H)-isoquinolinyl)-N-(4-fluo-rophenyl)-5,6-dimethyl-monohydrochloride) (YuHan); BY-112 (Altana); SPI-447 (Imidazo(1, 2-a)thieno(3,2-c)pyridin-3-amine, 5-methyl-2-(2-methyl-3- thieny-1) (Shinnippon); 3-hydroxymethyl-2methyl-9-phenyl-7H-8,9-dihydro-pyrano(2,-3-c)-imidazo(1,2-a) pyridine (PCT Publication WO 95/27714) (AstraZeneca); Pharmaprojects No. 4950 (3-hydroxymethyl-2-methyl-9-phenyl-7H-8,9-dihydro-1-pyrano(2,3-c)-imidazo(1,2-a) pyridine) (AstraZeneca, ceased) WO 95/27714; Pharmaprojects No. 4891 (EP 700899) (Aventis); Pharmaprojects No. 4697 (PCT Publication WO 95/32959) (AstraZeneca); H-335/25 (AstraZeneca); T-330 (Saitama 335) (Pharmacological Research Lab); Pharmaprojects No. 3177 (Roche); BY-574 (Altana); Pharmaprojects No. 2870 (Pfizer); AU-1421 (EP 264883) (Merck); AU-2064 (Merck); AY-28200 (Wyeth); Pharmaprojects No. 2126 (Aventis); WY-26769 (Wyeth); pumaprazole (PCT Publication WO 96/05199) (Altana); YH-1238 (YuHan); Pharmaprojects No. 5648 (PCT Publication WO 97/32854) (Dainippon); BY-686 (Altana); YM-020 (Yamanouchi); GYKI-34655 (Ivax); FPL-65372 (Aventis); Pharmaprojects No. 3264 (EP 509974) (AstraZeneca); nepaprazole (To a Eiyo); HN-11203 (Nycomed Pharma); OPC-22575; pumilacidin A (BMS); saviprazole (EP 234485) (Aventis); SKand F-95601 (GSK, discontinued); Pharmaprojects No. 2522 (EP 204215) (Pfizer); S-3337 (Aventis); RS-13232A (Roche); AU-1363 (Merck); SKand F-96067 (EP 259174) (Altana); SUN 8176 (Daiichi Phama); Ro-18-5362 (Roche); ufiprazole (EP 74341) (AstraZeneca); and Bay-p-1455 (Bayer); or a free base, free acid, salt, hydrate, ester, amide, enantiomer, isomer, tautomer, polymorph, prodrug, or derivative of these compounds.

Still other proton pump inhibitors contemplated by the present invention include those described in the following U.S. Pat. Nos. 4,628,098; 4,689,333; 4,786,505; 4,853,230; 4,965,269; 5,021,433; 5,026,560; 5,045,321; 5,093,132; 5,430,042; 5,433,959; 5,576,025; 5,639,478; 5,703,110; 5,705,517; 5,708,017; 5,731,006; 5,824,339; 5,855,914; 5,879,708; 5,948,773; 6,017,560; 6,123,962; 6,187,340; 6,296,875; 6,319,904; 6,328,994; 4,255,431; 4,508,905; 4,636,499; 4,738,974; 5,690,960; 5,714,504; 5,753,265; 5,817,338; 6,093,734; 6,013,281; 6,136,344; 6,183,776; 6,328,994; 6,479,075; 6,559,167.

Proton pump inhibitors as well as their salts, hydrates, esters, amides, enantiomers, isomers, tautomers, polymorphs, prodrugs, and derivatives may be prepared using standard procedures known to those skilled in the art of synthetic organic chemistry. See, e.g., March, Advanced Organic Chemistry: Reactions, Mechanisms and Structure, 4th Ed. (New York: Wiley-Interscience, 1992); Leonard et al., Advanced Practical Organic Chemistry (1992); Howarth et al., Core Organic Chemistry (1998); and Weisermel et al., Industrial Organic Chemistry (2002).

"Pharmaceutically acceptable salts," or "salts," include the salt of a proton pump inhibitor prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, algenic, beta.-hydroxybutyric, galactaric and galacturonic acids.

In one embodiment, acid addition salts are prepared from the free base forms using conventional methodology involving reaction of the free base with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like.

In other embodiments, an acid addition salt is reconverted to the free base by treatment with a suitable base. In a further embodiment, the acid addition salts of the proton pump inhibitors are halide salts, which are prepared using hydrochloric or hydrobromic acids. In still other embodiments, the basic salts are alkali metal salts, e.g., sodium salt.

Salt forms of proton pump inhibitors include, but are not limited to: a sodium salt form such as esomeprazole sodium, omeprazole sodium, rabeprazole sodium, pantoprazole sodium; or a magnesium salt form such as esomeprazole magnesium or omeprazole magnesium, described in U.S. Pat. No. 5,900,424; a calcium salt form; or a potassium salt form such as the potassium salt of esomeprazole, described in U.S. Pat. No. 6,511,996. Other salts of esomeprazole are described in U.S. Pat. Nos. 4,738,974 and 6,369,085. Salt forms of pantoprazole and lansoprazole are discussed in U.S. Pat. Nos. 4,758,579 and 4,628,098, respectively.

In one embodiment, preparation of esters involves functionalizing hydroxyl and/or carboxyl groups that may be present within the molecular structure of the drug. In another embodiment, the esters are acyl-substituted derivatives of free alcohol groups, e.g., moieties derived from carboxylic acids of the formula $RCOOR_1$ where $_1$ is a lower alkyl group. Esters can be reconverted to the free acids, if desired, by using conventional procedures such as hydrogenolysis or hydrolysis.

"Amides" may be prepared using techniques known to those skilled in the art or described in the pertinent literature. For example, amides may be prepared from esters, using suitable amine reactants, or they may be prepared from an anhydride or an acid chloride by reaction with an amine group such as ammonia or a lower alkyl amine.

"Tautomers" of substituted bicyclic aryl-imidazoles include, e.g., tautomers of omeprazole such as those described in U.S. Pat. Nos. 6,262,085; 6,262,086; 6,268,385; 6,312,723; 6,316,020; 6,326,384; 6,369,087; and 6,444,689.

An exemplary "isomer" of a substituted bicyclic aryl-imidazole is the isomer of omeprazole including but not limited to isomers described in: Oishi et al., Acta Cryst. (1989), C45, 1921-1923; U.S. Pat. No. 6,150,380; U.S. Patent Publication No. 02/0156284; and PCT Publication No. WO 02/085889.

Exemplary "polymorphs" include, but are not limited to, those described in PCT Publication No. WO 92/08716, and U.S. Pat. Nos. 4,045,563; 4,182,766; 4,508,905; 4,628,098; 4,636,499; 4,689,333; 4,758,579; 4,783,974; 4,786,505; 4,808,596; 4,853,230; 5,026,560; 5,013,743; 5,035,899; 5,045,321; 5,045,552; 5,093,132; 5,093,342; 5,433,959; 5,464,632; 5,536,735; 5,576,025; 5,599,794; 5,629,305; 5,639,478; 5,690,960; 5,703,110; 5,705,517; 5,714,504; 5,731,006; 5,879,708; 5,900,424; 5,948,773; 5,997,903; 6,017,560; 6,123,962; 6,147,103; 6,150,380; 6,166,213; 6,191,148; 5,187,340; 6,268,385; 6,262,086; 6,262,085; 6,296,875; 6,316,020; 6,328,994; 6,326,384; 6,369,085; 6,369,087; 6,380,234; 6,428,810; 6,444,689; and 6,462,0577.

In one embodiment, no portion of the proton pump inhibitor is enteric coated. In another embodiment, at least a portion of the proton pump inhibitor is not enteric coated. In another embodiment, at least a therapeutically effective portion of the proton pump inhibitor is not enteric coated. In another embodiment, at least about 5%, about 15%, about 20%, about 30%, about 400%, about 50% or about 60% of the proton pump inhibitor is not enteric coated.

In one embodiment, the proton pump inhibitor has a $D_{90}$, $D_{80}$, $D_{70}$ or $D_{50}$ particle size, by weight or by number, of less than about 500 µm, less than about 400 µm, less than about 300 µm, less than about 200 µm, less than about 150 µm, less than about 100 µm, less than about 80 µm, less than about 60 µm, less than about 40 µm, less than about 35 µm, less than about 30 µm, less than about 25 µm, less than about 20 µm, less than about 15 µm, or less than about 10 µm.

In another embodiment, compositions are provided wherein the micronized proton pump inhibitor is of a size which allows greater than about 90% or greater than about 75% of the proton pump inhibitor to be released from the dosage unit within about 1 hour, within about 50 minutes, within about 40 minutes, within about 30 minutes, within about 20 minutes, within about 10 minutes, or within about 5 minutes after placement in a standard dissolution test.

In another embodiment, compositions of the invention comprise one or more PPIs in a total amount of about 1 mg to about 3000 mg, about 1 mg to about 2000 mg, about 1 mg to about 1000 mg, about 5 mg to about 750 mg, about 5 mg to about 500 mg, about 5 mg to about 250 mg, about 5 mg to about 100 mg, about 5 mg to about 100 mg, or about 5 mg to about 50 mg, for example about 7.5 mg, about 10 mg, about 15 mg, about 20 mg or about 40 mg.

Compositions of the invention can be in the form of an orally deliverable dosage unit. The terms "oral administration" or "orally deliverable" herein include any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration.

Buffering Agent

Compositions of the invention comprise one or more pharmaceutically acceptable buffering agents. Buffering agents useful in the present invention include agents possessing pharmacological activity as a weak or strong base. In one embodiment, the buffering agent, when formulated with or administered substantially simultaneously with a PPI, functions to raise the pH of gastrointestinal fluid and thereby to substantially prevent or inhibit acid degradation of the PPI by gastrointestinal fluid for a period of time. In one embodiment, the period of time is a time sufficient to protect at least a therapeutic portion of the PPI from acid degradation in GI fluid.

In another embodiment, buffering agents useful in accordance with the present invention comprise a salt of a Group IA metal including, for example, a bicarbonate salt of a Group IA metal, a carbonate salt of a Group IA metal, an alkaline earth metal buffering agent, an amino acid, an alkaline salt of an amino acid, an aluminum buffering agent, a calcium buffering agent, a sodium buffering agent, or a magnesium buffering agent. Other suitable buffering agents include alkali (sodium and potassium) or alkaline earth (calcium and magnesium) carbonates, phosphates, bicarbonates, citrates, borates, acetates, phthalates, tartrates, succinates and the like, such as sodium or potassium phosphate, citrate, borate, acetate, bicarbonate and carbonate.

Non-limiting examples of suitable buffering agents include aluminum, magnesium hydroxide, aluminum hydroxide/magnesium hydroxide co-precipitate, aluminum hydroxide/sodium bicarbonate co-precipitate, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, L-arginine, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, tripotassium phosphate, trisodium phosphate, and trometamol. (Based in part upon the list provided in The Merck Index, Merck & Co. Rahway, N.J. (2001)). In addition, due to the ability of proteins or protein hydrolysates to react with stomach acids, they too can serve as buffering agents in the present invention. Furthermore, combinations or mixtures of the above mentioned buffering agents can be used in the pharmaceutical formulations described herein.

Buffering agents useful in the present invention also include buffering agents or combinations of buffering agents that interact with HCl (or other acids in the environment of interest) faster than the proton pump inhibitor interacts with the same acids. When placed in a liquid phase such as water, these buffering agents produce and maintain a pH greater than the pKa of the proton pump inhibitor.

In various other embodiments of the present invention, the buffering agent is present in a total amount of about 0.1 mEq/mg to about 5 mEq/mg of the proton pump inhibitor, about 0.5 mEq/mg to about 3 mEq/mg of the proton pump inhibitor, about 0.6 mEq/mg to about 2.5 mEq/mg of the proton pump inhibitor, about 0.7 mEq/mg to about 2.0 mEq/mg of the proton pump inhibitor, about 0.8 mEq/mg to about 1.8 mEq/mg of the proton pump inhibitor, about 1.0 mEq/mg to about 1.5 mEq/mg of the proton pump inhibitor. In another embodiment, the buffering agent is present in an amount of at least about 0.5 mEq/mg of the proton pump inhibitor, at least about 0.75 mEq/mg of the proton pump inhibitor, or at least about 1 mEq/mg of the proton pump inhibitor on a dry weight basis.

In another embodiment, one or more buffering agents are present in a total amount of about 0.5 mEq to about 160 mEq, about 1 mEq to about 150 mEq, about 10 mEq to about 150 mEq, about 10 mEq to about 75 mEq, about 10 mEq to about 60 mEq, or about 10 mEq to about 50 mEq. Illustratively, a composition of the invention can comprise about 1 mEq, or about 5 mEq, or about 10 mEq, or about 15 mEq, or about 20 mEq, or about 25 mEq, or about 30 mEq, or about 35 mEq, or about 40 mEq, or about 45 mEq, or about 50 mEq, or about 60 mEq, or about 70 mEq, or about 80 mEq, or about 90 mEq, or about 100 mEq, or about 110 mEq, or about 120 mEq, or about 130 mEq, or about 140 mEq, or about 150 mEq, or about 160 mEq of buffering agent.

In yet another embodiment, one or more buffering agents are present in a total amount of at least about 10 mEq, at least about 11 mEq, at least about 12 mEq, at least about 13 mEq, at least about 14 mEq, or at least about 15 mEq.

In still another embodiment, one or more buffering agents and the PPI are present in a weight ratio of at least about 5:1, at least about 7:1, at least about 10:1, at least about 20:1, greater than 20:1, at least about 21:1, at least about 22:1, at least about 23:1, at least about 25:1, at least about 30:1, at least about 35:1, at least about 40:1, greater than 40:1, or at least about 45:1.

In another embodiment, the amount of buffering agent present in a composition of the invention ranges from about 200 to about 3500 mg, about 300 to about 3000 mg, about 400 to about 2500 mg, or about 500 to about 2200 mg. In other embodiments, the amount of buffering agent present in a composition of the invention is about 200 mgs, or about 300 mgs, or about 400 mgs, or about 500 mgs, or about 600 mgs, or about 700 mgs, or about 800 mgs, or about 900 mgs, or about 1000 mgs, or about 1100 mgs, or about 1200 mgs, or about 1300 mgs, or about 1400 mgs, or about 1500 mgs, or about 1600 mgs, or about 1700 mgs, or about 1800 mgs, or about 1900 mgs, or about 2000 mgs, or about 2100 mgs, or about 2200 mgs, or about 2300 mgs, or about 2400 mgs, or about 2500 mgs, or about 2600 mgs, or about 2700 mgs, or about 2800 mgs, or about 2900 mgs, or about 3000 mgs, or about 3200 mgs, or about 3500 mgs.

In another embodiment, one or more buffering agents are present in a composition of the invention in a total amount that is greater than 800 mg, for example at least about 920 mg or at least about 1000 mg.

In still another embodiment, particularly where the composition is other than a dosage form selected from the group consisting of a suspension tablet, a chewable tablet, an effervescent powder, an effervescent tablet, lozenge and/or a troche, the buffering agent and PPI are present in a weight ratio greater than 20:1, not less than about 21:1, not less than about 22:1, not less than about 23:1, not less than about 24:1, not less than about 25:1, not less than about 26:1, not less than about 27:1, not less than about 28:1, not less than about 29:1, not less than about 30:1, not less than about 31:1, not less than about 32:1, not less than about 33:1, not less than about 34:1, not less than about 35:1, not less than about 36:1, not less than about 37:1, not less than about 38:1, not less than about 39:1, not less than about 40:1, not less than about 41:1, not less than about 42:1, not less than about 43:1, not less than about 44:1, not less than about 45:1, not less than about 46:1, not less than about 47:1, not less than about 48:1, not less than about 49:1, or not less than about 50:1.

In another embodiment, a composition is provided that comprises a combination of at least two non-amino acid buffering agents, wherein the combination of at least two non-amino acid buffering agents comprises substantially no aluminum hydroxide-sodium bicarbonate co-precipitate. In a related embodiment, if such a composition comprises a poly[phosphoryl/sulfon]-ated carbohydrate, the weight ratio of poly[phosphoryl/sulfon]-ated carbohydrate to buffering agent is less than 1:5 (0.2), less than 1:10 (0.1) or less than 1:20 (0.05). Alternatively, the poly[phosphoryl/sulfon]-ated carbohydrate is present in the composition, if at all, in an amount less than 50 mg, less than 25 mg, less than 10 mg or less than 5 mg.

In other embodiments, if the pharmaceutical composition comprises an amino acid buffering agent, the total amount of amino acid buffering agent present in the pharmaceutical composition is less than about 5 mEq, or less than about 4 mEq, or less than about 3 mEq.

The phrase "amino acid buffering agent" as used herein includes amino acids, amino acid salts, and amino acid alkali salts including: glycine, alanine, threonine, isoleucine, valine, phenylalanine, glutamic acid, asparagininic acid, lysine, aluminum glycinate and/or lysine glutamic acid salt, glycine hydrochloride, L-alanine, DL-alanine, L-threonine, DL-threonine, L-isoleucine, L-valine, L-phenylalanine, L-glutamic acid, L-glutamic acid hydrochloride, L-glutamic acid sodium salt, L-asparaginic acid, L-asparaginic acid sodium salt, L-lysine and L-lysine-L-glutamic acid salt. The term "non-amino acid buffering agent" herein includes buffering agents as defined hereinabove but does not include amino acid buffering agents.

In another embodiment, a composition of the invention comprises at least one non-amino acid buffering agent wherein the non-amino acid buffering agent is present in the composition in a total amount greater than 800 mg. In a related embodiment, if such a composition comprises a poly[phosphoryl/sulfon]-ated carbohydrate, the weight ratio of poly[phosphoryl/sulfon]-ated carbohydrate to buffering agent is less than 1:5 (0.2), less than 1:10 (0.1) or less than 1:20 (0.05). Alternatively, the poly[phosphorylsulfon]-ated carbohydrate is present in the composition, if at all, in an amount less than 50 mg, less than 25 mg, less than 10 mg or less than 5 mg.

In still another embodiment, a composition is provided which comprises at least one buffering agent in a total amount of at least about 10 mEq. In a related embodiment, if an amino acid buffering agent is present in the composition, at least one of the following conditions is met: (1) the weight ratio of amino acid buffering agent:proton pump inhibitor is greater than 20:1; (2) the composition comprises at least two non-amino acid buffering agents; (3) the composition comprises at least one non-amino acid buffering agent wherein the weight ratio of the at least one non-amino acid buffering agent:proton pump inhibitor is greater than 20:1; and/or (4) the weight ratio of total buffering agent:proton pump inhibitor is greater than 40:1.

In other embodiments, where two or more buffering agents are present, the two or more buffering agents comprise at least two non-amino acid buffering agents, wherein the combination of at least two non-amino acid buffering agents comprises substantially no aluminum hydroxide-sodium bicarbonate co-precipitate.

In still another embodiment, the buffering agent comprises a mixture of sodium bicarbonate, calcium carbonate, and magnesium hydroxide, wherein the sodium bicarbonate, calcium carbonate, and magnesium hydroxide are each present in an amount of about 0.1 mEq/mg proton pump inhibitor to about 5 mEq/mg of the proton pump inhibitor.

Also provided herein are pharmaceutical compositions comprising at least one soluble buffering agent. The term "soluble buffering agent" as used herein refers to an antacid that has a solubility of at least about 500 mg/mL, or at least about 300 mg/mL, or at least about 200 mg/mL, or at least about 100 mL/mL in gastrointestinal fluid or simulated gastrointestinal fluid.

In some embodiments of the present invention, the buffering agent has a defined particle size distribution. For example, in one embodiment, the $D_{50}$, $D_{70}$, $D_{80}$, or $D_{90}$ particle size of the buffering agent, by weight or by number, is no greater than about 20 µm, no greater than about 30 µm, no greater than about 40 µm, no greater than about 50 µm, no greater than about 60 µm, no greater than about 70 µm, no greater than about 80 µm, no greater than about 90 µm, no greater than about 100 µm in diameter, no greater than about 200 µm in diameter, no greater than about 300 µm in diameter, no greater than about 400 µm in diameter, or no greater than about 100 µm in diameter.

Pharmaceutical Excipients

Compositions of the invention can, if desired, include one or more pharmaceutically acceptable excipients. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition. Excipients include, by way of illustration and not limitation, diluents, disintegrants, binding agents, adhesives, wetting agents, lubricants, glidants, surface modifying agents, substances added to mask or counteract a disagreeable taste or odor, flavors, dyes, fragrances, and substances added to improve appearance of the composition. Any such excipients can be used in any dosage forms of according to the present invention, including liquid, solid or semi-solid dosage forms.

Excipients optionally employed in compositions of the invention can be solids, semi-solids, liquids or combinations thereof. Compositions of the invention containing excipients can be prepared by any known technique of pharmacy that comprises admixing an excipient with a drug or therapeutic agent.

Compositions of the invention optionally comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; and the like. Such diluents, if present, constitute in total about 5% to about 99%, about 10% to about 85%, or about 20% to about 80%, of the total weight of the composition. The diluent or diluents selected preferably exhibit suitable flow properties and, where tablets are desired, compressibility.

The use of extragranular microcrystalline cellulose (that is, microcrystalline cellulose added to a wet granulated composition after a drying step) can be used to improve hardness (for tablets) and/or disintegration time.

Compositions of the invention optionally comprise one or more pharmaceutically acceptable disintegrants as excipients, particularly for tablet formulations. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, xanthan, locust bean, karaya, pectin and tragacanth gums.

Disintegrants may be added at any suitable step during the preparation of the composition, particularly prior to a granulation step or during a lubrication step prior to compression. Such disintegrants, if present, constitute in total about 0.2% to about 30%, about 0.2% to about 10%, or about 0.2% to about 5%, of the total weight of the composition.

Croscarmellose sodium is a preferred disintegrant for tablet or capsule disintegration, and, if present, typically constitutes about 0.2% to about 10%, about 0.2% to about 7%, or about 0.2% to about 5%, of the total weight of the composition.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, about 0.75% to about 15%, or about 1% to about 10%, of the total weight of the composition.

Compositions of the invention optionally comprise one or more pharmaceutically acceptable wetting agents as excipients. Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the composition.

Compositions of the invention optionally comprise one or more pharmaceutically acceptable lubricants (including anti-adherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition.

Suitable anti-adherents include talc, cornstarch, DL-leucine, sodium lauryl sulfate and metallic stearates. Talc is a anti-adherent or glidant used, for example, to reduce formulation sticking to equipment surfaces and also to reduce static in the blend. Talc, if present, constitutes about 0.1% to about 10%, about 0.25% to about 5%, or about 0.5% to about 2%, of the total weight of the composition.

Glidants can be used to promote powder flow of a solid formulation. Suitable glidants include colloidal silicon dioxide, starch, talc, tribasic calcium phosphate, powdered cellulose and magnesium trisilicate. Colloidal silicon dioxide is particularly preferred.

Compositions of the present invention can comprise one or more anti-foaming agents. Simethicone is an illustrative anti-foaming agent.

Compositions of the present invention can comprise one or more flavoring agents, sweetening agents, and/or colorants. Flavoring agents useful in the present invention include, without limitation, acacia syrup, alitame, anise, apple, aspartame, banana, Bavarian cream, berry, black currant, butter, butter pecan, butterscotch, calcium citrate, camphor, caramel, cherry, cherry cream, chocolate, cinnamon, citrus, citrus punch, citrus cream, cocoa, coffee, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, MagnaSweet®, maltol, mannitol, maple, menthol, mint, mint cream, mixed berry, nut, orange, peanut butter, pear, peppermint, peppermint cream, Prosweet® Powder, raspberry, root beer, rum, saccharin, safrole, sorbitol, spearmint, spearmint cream, strawberry, strawberry cream, stevia, sucralose, sucrose, Swiss cream, tagatose, tangerine, thaumatin, tutti fruitti, vanilla, walnut, watermelon, wild cherry, wintergreen, xylitol, and combinations thereof, for example, anise-menthol, cherry-anise, cinnamon-orange, cherry-cinnamon, chocolate-mint, honey-lemon, lemon-lime, lemon-mint, menthol-eucalyptus, orange-cream, vanilla-mint, etc.

Sweetening agents that can be used in the present invention include, for example, acesulfame potassium (acesulfame K), alitame, aspartame, cyclamate, cylamate, dextrose, isomalt, MagnaSweet®, maltitol, mannitol, neohesperidine DC, neotame, Prosweet® Powder, saccharin, sorbitol, stevia, sucralose, sucrose, tagatose, thaumatin, xylitol, and the like.

The foregoing excipients can have multiple roles as is known in the art. For example, starch can serve as a filler as well as a disintegrant. The classification of excipients above is not to be construed as limiting in any manner.

Pharmaceutical Dosage Forms

Compositions of the present invention can be formulated as solid, liquid or semi-solid dosage forms. In one embodiment, such compositions are in the form of discrete dose units or dosage units. The terms "dose unit" and/or "dosage unit" herein refer to a portion of a pharmaceutical composition that contains an amount of a therapeutic agent suitable for a single administration to provide a therapeutic effect. Such dosage units may be administered one to a small plurality (i.e. 1 to about 4) of times per day, or as many times as needed to elicit a therapeutic response. A particular dosage form can be selected to accommodate any desired frequency of administration to achieve a specified daily dose. Typically one dose unit, or a small plurality (i.e. up to about 4) of dose units, provides a sufficient amount of the active drug (e.g. benzimidazole moiety) to result in the desired response or effect.

Alternatively, compositions of the invention can also be formulated for rectal, topical, or parenteral (e.g. subcutaneous, intramuscular, intravenous and intradermal or infusion) delivery.

In one embodiment, compositions of the invention are suitable for rapid onset of therapeutic effect, particularly with respect to the PPI component. In another embodiment, upon oral administration of a composition of the invention to a subject, at least a therapeutically effective amount of the PPI is available for absorption in the stomach of the subject. As discussed above, most commercially available PPIs require enteric coating to prevent exposure of the PPI to gastrointestinal fluids (and consequent drug degradation) by way of pH dependent coatings. Such coating, in turn, prevents rapid PPI absorption and therapeutic onset of action. Compositions of the present invention, by contrast, do not require enteric coating to maintain drug stability in gastrointestinal fluids and thereby provide for rapid absorption and onset of therapeutic effect. In fact, in one embodiment, a composition comprises at least a therapeutically effective amount of PPI that is not enteric coated.

In one embodiment, a single dosage unit, be it solid or liquid, comprises a therapeutically effective amount or a therapeutically and/or prophylactically effective amount of PPI. The term "therapeutically effective amount" or "therapeutically and/or prophylactically effective amount" as used herein refers to an amount of compound or agent that is sufficient to elicit the required or desired therapeutic and/or prophylactic response, as the particular treatment context may require.

It will be understood that a therapeutically and/or prophylactically effective amount of a drug for a subject is dependent inter alia on the body weight of the subject. A "subject" herein to which a therapeutic agent or composition thereof can be administered includes a human subject of either sex and of any age, and also includes any nonhuman animal, particularly a domestic or companion animal, illustratively a cat, dog or a horse.

Solid Dosage Forms

In some embodiments, compositions of the invention are in the form of solid dosage forms or units. Non-limiting examples of suitable solid dosage forms include tablets (e.g. suspension tablets, bite suspension tablets, rapid dispersion tablets, chewable tablets, effervescent tablets, bilayer tablets, etc), caplets, capsules (e.g. a soft or a hard gelatin capsule), powder (e.g. a packaged powder, a dispensable powder or an effervescent powder), lozenges, sachets, cachets, troches, pellets, granules, microgranules, encapsulated microgranules, powder aerosol formulations, or any other solid dosage form reasonably adapted for oral administration.

Tablets are an illustrative dosage form for compositions of the invention. Tablets can be prepared according to any of the many relevant, well known pharmacy techniques. In one embodiment, tablets or other solid dosage forms can be prepared by processes that employ one or a combination of methods including, without limitation, (1) dry mixing, (2) direct compression, (3) milling, (4) dry or non-aqueous granulation, (5) wet granulation, or (6) fusion.

The individual steps in the wet granulation process of tablet preparation typically include milling and sieving of the ingredients, dry powder mixing, wet massing, granulation and final grinding. Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). Typically, no wet binder or moisture is involved in any of the steps.

In another embodiment, solid dosage forms such as tablets can be prepared by mixing a PPI with at least one buffering agent as described herein above and, if desired, with one or more optional pharmaceutical excipient to form a substantially homogeneous preformulation blend. The preformulation blend can then be subdivided and optionally further processed (e.g. compressed, encapsulated, packaged, dispersed, etc.) into any desired dosage forms.

Compressed tablets can be prepared by compacting a powder or granulation composition of the invention. The term "compressed tablet" generally refers to a plain, uncoated tablet suitable for oral ingestion, prepared by a single compression or by pre-compaction tapping followed by a final compression. Tablets of the present invention may be coated or otherwise compounded to provide a dosage form affording the advantage of improved handling or storage characteristics. Preferably, however, any such coating will be selected so as to not substantially delay onset of therapeutic effect of a composition of the invention upon administration to a subject. The term "suspension tablet" as used herein refers to a compressed tablet that rapidly disintegrates after placement in water.

In one embodiment, a composition of the invention comprises a multi-layer tablet having a core comprising a proton pump inhibitor; the core is substantially or completely surrounded by the buffering agent. In one such embodiment, the buffering agent layer completely surrounds the core. In another embodiment, the buffering agent layer partially surrounds the core. In yet another embodiment, the buffering agent layer is in contact with a portion of or with all of the surface area of the core.

In another embodiment, one or more intermediate layers exists in between the core and the buffering agent. The intermediate layers can comprise any pharmaceutically acceptable material, preferably inert and non-pH sensitive coating materials such as polymer based coatings.

In still another embodiment, compositions of the invention can be microencapsulated, for example as is described in U.S. Patent Publication No. 2005/0037070, hereby incorporated by reference herein in its entirety.

In another embodiment, a composition of the invention comprises a proton pump inhibitor and a buffering agent mixed together in powder form and optionally filled into a capsule, for example a hard or soft gelatin or HPMC capsule.

Liquid Dosage Forms

In another embodiment of the invention, compositions can be in the form of liquid dosage forms or units. Non-limiting examples of suitable liquid dosage forms include solutions, suspension, elixirs, syrups, liquid aerosol formulations, etc.

In one embodiment, a liquid composition comprising water, PPI and a buffering agent can be prepared. In another embodiment, compositions of the invention are in the form of a powder for suspension that can be suspended in a liquid vehicle prior to administration to a subject. While the powder for suspension itself, can be a solid dosage form of the present invention, the powder dispersed in liquid also comprises a liquid embodiment of the invention.

Generally, a liquid composition of PPI (without a buffering agent) would exhibit a very short period of stability, even when maintained under refrigerated conditions. This is particularly inconvenient in the hospital setting as fresh batches of suspension are continually required.

Suspension compositions of the invention comprise at least one PPI, a buffering agent, a liquid media (e.g. water, de-ionized water, etc.) and one or more optional pharmaceutical excipients. Such compositions, upon storage in a closed container maintained at either room temperature, refrigerated (e.g. about 5-10° C.) temperature, or freezing temperature for a period of about 1, 2, 3, 4, 5, 6, 7, 8, 9, 10, 11, or 12 months, exhibit at least about 90%, at least about 92.5%, at least about 95%, or at least about 97.5% of the original PPI present therein.

Storage Stability

In one embodiment, compositions of the invention are in the form of a powder for suspension that is ultimately to be suspended in a liquid vehicle prior to administration to a subject. Liquid compositions comprising an acid labile PPI suspended in a liquid vehicle, without more, would typically exhibit short periods of stability, even when maintained under refrigerated conditions. This is particularly inconvenient in the hospital setting as fresh batches of suspension are continually required. Suspension compositions of the invention are believed to exhibit improve storage stability.

Illustrative suspension compositions of the invention comprise at least one PPI, at least one buffering agent, vitamin $B_{12}$, water, and one or more optional pharmaceutical excipients. Such compositions, upon storage in a closed container maintained at room temperature, refrigerated (e.g. about 5 to about 5-10° C.) temperature, or frozen for a period of about 1, 2, 3, 4, 5, 6, 7, 8, 9, 10, 11, or 12 months, preferably exhibit at least about 90%, more preferably at least about 92.5%, still more preferably at least about 95%, and yet more preferably at least about 97.5% of the proton pump inhibitor present therein.

Parietal Cell Activators

In one embodiment, a composition of the present invention can further include one or more parietal cell activators. Parietal cell activators are particularly preferred where the benzimidazole moiety is a PPI. Parietal cell activators such as chocolate, calcium and sodium bicarbonate and other alkaline substances stimulate the parietal cells and enhance the pharmacologic activity of the PPI administered. For the purposes of this application, "parietal cell activator" or "activator" shall mean any compound or mixture of compounds possessing such stimulatory effect including, but not limited to, chocolate, sodium bicarbonate, calcium (for example, calcium carbonate, calcium gluconate, calcium hydroxide, calcium acetate and calcium glycerophosphate), peppermint oil, spearmint oil, coffee, tea and colas (even if decaffeinated), caffeine, theophylline, theobromine, and amino acids (particularly aromatic amino acids such as phenylalanine and tryptophan) and combinations thereof.

Parietal cell activators, if desired, are typically present in a composition of the invention in an amount sufficient to produce the desired stimulatory effect without causing untoward side effects to patients. For example, chocolate, as raw cocoa, is administered in an amount of about 5 mg to 2.5 g per 20 mg dose of omeprazole (or equivalent pharmacologic dose of another proton pump inhibiting agent). The dose of activator administered to a subject, for example, a human, in the context of the present invention should be sufficient to result in enhanced effect of a PPI over a desired time frame.

Illustratively, the approximate effective ranges for various parietal cell activators per 20 mg dose of omeprazole (or equivalent dose of other PPI) include, Chocolate (raw cocoa)—5 mg to 2.5 g; Sodium bicarbonate—7 mEq to 25 mEq; Calcium carbonate—1 mg to 1.5 g; Calcium gluconate—1 mg to 1.5 g; Calcium lactate—1 mg to 1.5 g; Calcium hydroxide—1 mg to 1.5 g; Calcium acetate—0.5 mg to 1.5 g; Calcium glycerophosphate—0.5 mg to 1.5 g; Peppermint oil—(powdered form) 1 mg to 1 g; Spearmint oil—(powdered form) 1 mg to 1 g; Coffee—20 ml to 240 ml; Tea—20 ml to 240 ml; Cola—20 ml to 240 ml; Caffeine—0.5 mg to 1.5 g; Theophylline—0.5 mg to 1.5 g; Theobromine—0.5 mg to 1.5 g; Phenylalanine—0.5 mg to 1.5 g; and Tryptophan—0.5 mg to 1.5 g.

Administration

Compositions of the present invention are useful for treating and/or preventing, inter alia, gastrointestinal disorders and, in particular, acid related gastrointestinal disorders. The phrase "acid related gastrointestinal disorder" or "acid related gastrointestinal disease" refers generally to a disease or disorder that occurs due to an imbalance between acid and pepsin production on the one hand, so-called aggressive factors, and mucous, bicarbonate, and prostaglandin production on the other hand, so-called defensive factors.

The term "treat" or "treatment" as used herein refers to any treatment of a disorder or disease associated with a gastrointestinal disorder, and includes, but is not limited to, inhibiting the disorder or disease, for example, arresting the development of the disorder or disease; relieving the disorder or disease, for example, causing regression of the disorder or disease; or relieving the condition caused by the disease or disorder, for example, stopping the symptoms of the disease or disorder.

The term "prevent" or "prevention," in relation to a gastrointestinal disorder or disease, means preventing the onset of gastrointestinal disorder or disease development if none had occurred, or preventing further gastrointestinal disorder or disease development if the gastrointestinal disorder or disease was already present.

In mammals gastrointestinal disorders include, but are not limited to, duodenal ulcer, gastric ulcer, acid dyspepsia, gastroesophageal reflux disease (GERD), severe erosive esophagitis, poorly responsive symptomatic gastroesophageal reflux disease, (acid reflux), heartburn, nighttime heartburn symptoms, nocturnal acid breakthrough (NAB), and gastrointestinal pathological hypersecretory conditions such as Zollinger Ellison Syndrome. Illustrative acid-related gastrointestinal disorders including duodenal ulcer disease, gastric ulcer disease, gastroesophageal reflux disease (GERD), erosive esophagitis, poorly responsive symptomatic gastroesophageal reflux disease (acid reflux), pathological gastrointestinal hypersecretory disease, Zollinger Ellison Syndrome, acid dyspepsia, heartburn, and/or NSAID induced ulcer.

Where the disorder is heartburn, the heartburn can be meal-related or induced, sleep-related or induced, and/or nighttime-related or induced heartburn. Sleep-related heartburn and/or nighttime-related heartburn can be caused, for example, by breakthrough gastritis between conventional doses of a therapeutic agent, such as while sleeping or in the early morning hours after a night's sleep. Treatment of these conditions is accomplished by administering to a subject a gastrointestinal-disorder-effective amount (or a therapeutically-effective amount) of a pharmaceutical composition according to the present invention. A subject may be experiencing one or more of the above conditions or disorders or related symptoms.

Compositions of the invention can be administered to a subject at any suitable time, for example upon waking, prior to a meal, during the day, or at night time (e.g. before bed). In one embodiment, a composition of the invention is useful for treating and/or preventing nighttime heartburn or nighttime heartburn symptoms, nocturnal acid breakthrough (NAB), and/or for providing nighttime pH control. NAB herein refers to intragastric pH less than 4 for more than 1 hour in the overnight period.

In another embodiment, a composition of the invention is administered to a subject between about 6:00 pm and about 1:00 am, about 7:00 pm and about 1:00 am, about 8:00 pm and about 12:00 am, about 8:00 pm and about 11:pm, about 8:00 pm and about 10:30 pm, or about 9:00 pm and about 10:30 pm, for example at about 9:00 pm, 9:15 pm, 9:30 pm, 9:45 pm, 10:00 pm, 10:15 pm or 10:30 pm.

In another embodiment, a composition of the invention is administered to a subject within about 3 hours before or after the subject has eaten dinner, within about 2 hours before or after the subject has eaten dinner, within about 1 hour before or after the subject has eaten dinner or within about 30 minutes before or after the subject has eaten dinner.

In another embodiment, a composition of the invention is administered to a subject at such a time to result in a blood serum concentration of the proton pump inhibitor of at least about 0.1 micromolar, at least about 0.2 micromolar, at least about 0.3 micromolar, at least about 0.4 micromolar, at least about 0.5 micromolar, at least about 0.6 micromolar, at least about 0.7 micromolar, at least about 0.8 micromolar, at least about 0.9 micromolar that occurs at any time during the subject's typical period of nocturnal acid breakthrough, for example the subject's next typical period of nocturnal acid breakthrough following administration.

The term "the subject's typical period of nocturnal acid breakthrough" refers to a period of time at night during which a subject tends to experience intragastric pH not greater than 4 for a continuous period of about one hour. This can be determined, for example, by measuring a subject's intragastric pH for 1 to 3 nights and calculating the beginning and ending times (of pH less than 4), or the average beginning and ending times if pH is measured during more than 1 night. For example, if a subject experiences nocturnal acid breakthrough on a first measured day starting at 1:00 am and ending at 4:00 am, and on a second measured day that subject experiences nocturnal acid breakthrough starting at 2:00 am and ending at 5:00 am, the subject's typical period of nocturnal acid breakthrough could be characterized as 1:30 am to 4:30 am. Thus, a composition of the invention could be administered to the subject at such a time so as to provide a blood serum concentration of the proton pump inhibitor of at least about 0.1 micromolar, at least about 0.2 micromolar, at least about 0.3 micromolar, at least about 0.4 micromolar, at least about 0.5 micromolar, at least about 0.6 micromolar, at least about 0.7 micromolar, at least about 0.8 micromolar, or at least about 0.9 micromolar at any time during the period of about 12:00 am to about 6:00 am, about 12:30 am to about 5:30 am, about 1:00 am to about 5:00 am, or about 2:00 am to about 4:00 am following administration.

In another embodiment, a composition of the invention is administered to a subject at such a time to result in a blood serum concentration of the proton pump inhibitor of at least about 0.1 micromolar, at least about 0.2 micromolar, at least about 0.3 micromolar, at least about 0.4 micromolar, at least about 0.5 micromolar, at least about 0.6 micromolar, at least about 0.7 micromolar, at least about 0.8 micromolar, at least about 0.9 micromolar or at least about 1 micromolar continuously throughout the subject's typical period of nocturnal acid breakthrough, for example the subject's next typical period of nocturnal acid breakthrough after administration.

In another embodiment, a composition of the invention is administered to a subject at such a time to result in a blood serum concentration of the proton pump inhibitor of at least about 0.1 micromolar, at least about 0.2 micromolar, at least about 0.3 micromolar, at least about 0.4 micromolar, at least about 0.5 micromolar, at least about 0.6 micromolar, at least about 0.7 micromolar, at least about 0.8 micromolar, at least about 0.9 micromolar, or at least about 1 micromolar at any time point during the period of about 12:00 am to about 6:00 am, about 12:30 am to about 5:30 am, about 1:00 am to about 5:00 am, or about 2:00 am to about 4:00 am following administration.

The term "following administration" in the context of timing of administration means the next relevant time period after administration. For example, if a composition of the invention is to be administered to a subject at such a time to result in a blood serum concentration of the proton pump inhibitor of about 0.1 micromolar to about 5 micromolar at any time point from about 12:00 am to about 6:00 am following administration, that refers to the next 12:00 am to 6:00 am period following administration. If the composition was administered at 10:00 pm on Day 1, the period of about 12:00 am to about 6:00 am following administration refers to 12:0 am to about 6:00 am on the day immediately following Day 1.

In another embodiment, a composition of the invention is administered to a subject at such a time to result in a blood serum concentration of the proton pump inhibitor of at least about 0.1 micromolar, at least about 0.2 micromolar, at least about 0.3 micromolar, at least about 0.4 micromolar, at least about 0.5 micromolar, at least about 0.6 micromolar, at least about 0.7 micromolar, at least about 0.8 micromolar, at least about 0.9 micromolar or at least about 1 micromolar continuously from about 12:00 am to about 6:00 am, from about 12:30 am to about 5:30 am, from about 1:00 am to about 5:00 am, or from about 2:00 am to about 4:00 am following administration.

In another embodiment, a composition of the invention is administered to a subject at such a time to result in a blood serum concentration of the proton pump inhibitor of about 0.1 micromolar to about 5 micromolar, about 0.2 micromolar to about 2.5 micromolar, or about 0.3 micromolar to about 2 micromolar continuously from about 12:00 am to about 6:00 am, from about 12:30 am to about 5:30 am, from about 1:00 am to about 5:00 am, or from about 2:00 am to about 4:00 am following administration.

In another embodiment, a composition of the invention is administered to a subject at such a time to result in a blood serum concentration of the proton pump inhibitor of about 0.1 micromolar to about 5 micromolar, about 0.2 micromolar to about 2.5 micromolar, or about 0.3 micromolar to about 2 micromolar from about 12:00 am to about 6:00 am, from about 12:30 am to about 5:30 am, at any time during the period of about 1:00 am to about 5:00 am, or from about 2:00 am to about 4:00 am following administration.

In still another embodiment, a composition of the invention is administered to a subject at such a time to result in a $C_{max}$ of the proton pump inhibitor that occurs during the subject's typical period of nocturnal acid breakthrough, for example during the subject's typical period of nocturnal acid breakthrough following administration.

In another embodiment, a composition of the invention is administered to a subject at such a time to result in a $C_{max}$ of the proton pump inhibitor that occurs about 0.1 to about 5 hours, about 0.1 to about 4 hours, about 0.1 to about 3 hours, or about 0.1 to about 2 hours before the subject's typical period of nocturnal acid breakthrough, for example during the subject's typical period of nocturnal acid breakthrough following administration.

Castell, Donald et al., *Zegerid Oral Suspension is More Effective than Pantoprazole (Protonix) Delayed-Release Capsules in Reducing Nighttime Gastric Acidity in GERD Patients*, American Journal of Gastroenterology, Vol 99, No. 10 S40 is hereby incorporated by reference herein in its entirety.

Compositions of the invention are to be administered and dosed in accordance with good medical practice, taking into account the clinical condition of the individual patient, the site and method of administration, scheduling of administration and other factors known to medical practitioners. In human therapy, it is important to provide a dosage form that delivers the required therapeutic amount of the drug in vivo, and renders the drug bioavailable in a rapid manner. In addition to the dosage forms described herein, the dosage forms described by Phillips et al. in U.S. Pat. No. 6,489,346 are incorporated herein by reference.

The percent of intact drug that is absorbed into the bloodstream is not narrowly critical, as long as a therapeutic-disorder-effective amount, for example a gastrointestinal-disorder-effective amount of a proton pump inhibiting agent, is absorbed following administration of the pharmaceutical composition to a subject. It will be understood that the amount of proton pump inhibiting agent and/or antacid that is administered to a subject is dependent on various factors including the sex, general health, diet, and/or body weight of the subject.

Illustratively, when administering a PPI to a young child or a small animal, such as a dog, a relatively low amount of the proton pump inhibitor, e.g., about 1 mg to about 30 mg, will often provide blood serum concentrations consistent with therapeutic effectiveness. Where the subject is an adult human or a large animal, such as a horse, achievement of a therapeutically effective blood serum concentration may require larger dosage units, for example about 10 mg, about 15 mg, about 20 mg, about 30 mg, about 40 mg, about 80 mg, or about 120 mg dose for an adult human, or about 150 mg, or about 200 mg, or about 400 mg, or about 800 mg, or about 1000 mg dose, or about 1500 mg dose, or about 2000 mg dose, or about 2500 mg dose, or about 3000 mg dose, or about 3200 mg dose, or about 3500 mg dose for an adult horse.

In various other embodiments of the present invention, the amount of proton pump inhibitor administered to a subject is about 1-2 mg/Kg of body weight, illustratively about 0.5 mg/Kg of body weight, about 1 mg/Kg of body weight, about 1.5 mg/Kg of body weight, or about 2 mg/Kg of body weight.

Treatment dosages generally may be titrated to optimize safety and efficacy. Typically, dosage-effect relationships from in vitro and/or in vive tests initially can provide useful guidance on the proper doses for subject administration. Studies in animal models generally may be used for guidance regarding effective dosages for treatment of gastrointestinal disorders or diseases in accordance with the present invention. In terms of treatment protocols, it should be appreciated that the dosage to be administered will depend on several factors, including the particular agent that is administered, the route chosen for administration, and the condition of the particular subject.

In another embodiment of the present invention, the composition is administered to a subject in an amount sufficient to achieve a measurable serum concentration of a non-acid degraded or non-acid reacted proton pump inhibitor greater than about 100 ng/ml within about 30 minutes or about 15 minutes or about 10 minutes after administration of the composition.

In another embodiment of the present invention, the composition is administered to a subject in an amount sufficient to achieve a measurable serum concentration of the proton pump inhibitor greater than about 150 ng/ml within about 15 minutes and to maintain a serum concentration of the proton pump inhibitor of greater than about 150 ng/ml from about 15 minutes to about 1 hour after administration of the composition. In yet another embodiment of the present invention, the composition is administered to the subject in an amount sufficient to achieve a measurable serum concentration of the proton pump inhibitor greater than about 250 ng/ml within about 15 minutes and to maintain a serum concentration of the proton pump inhibiting agent of greater than about 150 ng/ml from about 15 minutes to about 1 hour after administration of the composition.

In another embodiment of the present invention, the composition is administered to the subject in an amount sufficient to achieve a measurable serum concentration of the proton pump inhibitor greater than about 350 ng/ml within about 15 minutes and to maintain a serum concentration of the proton pump inhibitor of greater than about 150 ng/ml from about 15 minutes to about 1 hour after administration of the composition. In another embodiment, the composition is administered to the subject in an amount sufficient to achieve a measurable serum concentration of the proton pump inhibiting agent greater than about 450 ng/ml within about 15 minutes and to maintain a serum concentration of the proton pump inhibiting agent of greater than about 150 ng/ml from about 15 minutes to about 1 hour after administration of the composition.

In another embodiment, the composition is administered to the subject in an amount sufficient to achieve a measurable serum concentration of the proton pump inhibitor greater than about 150 ng/ml within about 30 minutes and to maintain a serum concentration of the proton pump inhibitor of greater than about 150 ng/ml from about 30 minutes to about 1 hour after administration of the composition. In yet another embodiment of the present invention, the composition is administered to the subject in an amount to achieve a measurable serum concentration of the proton pump inhibitor greater than about 250 ng/ml within about 30 minutes and to maintain a serum concentration of the proton pump inhibitor of greater than about 150 ng/ml from about 30 minutes to about 1 hour after administration of the composition. In another embodiment of the present invention, the composition is administered to the subject in an amount sufficient to achieve a measurable serum concentration of the proton pump inhibitor greater than about 350 ng/ml within about 30 minutes and to maintain a serum concentration of the proton pump inhibitor of greater than about 150 ng/ml from about 30 minutes to about 1 hour after administration of the composition. In another embodiment of the present invention, the composition is administered to the subject in an amount sufficient to achieve a measurable serum concentration of the proton pump inhibitor greater than about 450 ng/ml within about 30 minutes and to maintain a serum concentration of the proton pump inhibiting agent of greater than about 150 ng/ml from about 30 minutes to about 1 hour after administration of the composition.

In still another embodiment of the present invention, the composition is administered to the subject in an amount sufficient to achieve a measurable serum concentration of a non-acid degraded or non-acid reacted proton pump inhibitor greater than about 500 ng/ml within about 1 hour after administration of the composition. In yet another embodiment of the present invention, the composition is administered to the subject in an amount to achieve a measurable serum concentration of a non-acid degraded or non-acid reacted proton pump inhibitor greater than about 300 ng/ml within about 45 minutes after administration of the composition.

Contemplated compositions of the present invention provide a therapeutic effect as proton pump inhibiting agent medications over an interval of about 5 minutes to about 24 hours after administration, enabling, for example, once-a-day, twice-a-day, or three times a day administration if desired.

In another embodiment, upon oral administration of a composition of the invention to a plurality of fasted human subjects, the subjects exhibit an average $T_{max}$ of PPI within about 30 seconds to about 90 minutes, within about 1 minute to about 80 minutes, within about 5 minutes to about 60 minutes, within about 10 minutes to about 50 minutes, or within about 15 minutes to about 45 minutes.

In still another embodiment, upon administration of a composition of the invention to a plurality of fasted human subjects, the subjects exhibit an average plasma concentration of the PPI of at least about 0.1 µg/ml, at least about 0.15 µg/ml, at least about 0.2 µg/ml, at least about 0.3 µg/ml, at least about 0.4 µg/ml, at least about 0.5 µg/ml, at least about 0.6 µg/ml, at least about 0.7 µg/ml, at least about 0.8 µg/ml, at least about 0.9 µg/ml, at least about 1 µg/ml, at least about 1.5 µg/ml, or at least about 2.0 µg/ml at any time within about 90 minutes, within about 75 minutes, within about 60 minutes, within about 55 minutes, within about 50 minutes, within about 45 minutes, within about 40 minutes, within about 35 minutes, within about 30 minutes, within about 25 minutes, within about 20 minutes, within about 17 minutes, within about 15 minutes, within about 12 minutes, or within about 10 minutes after administration.

In yet another embodiment, upon administration of a composition of the invention to a plurality of fasted human subjects, the subjects exhibit a plasma concentration of PPI of at least about 0.1 µg/ml, at least about 0.15 µg/ml, at least about 0.2 µg/ml, at least about 0.3 µg/ml, at least about 0.4 µg/ml, at least about 0.5 µg/ml, at least about 0.6 µg/ml, at least about 0.7 µg/ml, at least about 0.8 µg/ml, at least about 0.9 µg/ml, at least about 1.0 µg/ml, at least about 1.5 µg/ml or at least about 2.0 µg/ml, maintained from at latest about 15 minutes to at earliest about 60 minutes after administration, preferably at latest about 15 minutes after administration to at earliest about 90 minutes after administration, more preferably at latest about 15 minutes to at earliest about 120 minutes after administration, and still more preferably at latest about 15 minutes to at earliest about 180 minutes after administration.

In another embodiment, upon administration of a composition of the invention to a plurality of fasted human subjects, the subjects exhibit at least one of: a mean $C_{max}$ of PPI of about 500 µg/ml to about 2000 µg/ml, about 600 µg/ml to about 1900 µg/ml, or about 700 ng/ml to about 1800 µg/ml; a mean $T_{max}$ of PPI of about 0.15 to about 2 hours, about 0.25 to about 1.75 hours, or about 0.3 hours to about 1 hour; and/or a mean $AUC_{(0-inf)}$ of PPI of about 1000 to about 3000 µg·hr/ml, about 1500 to about 2700 µg·hr/ml, or about 1700 to about 2500 µg·hr/ml.

In another embodiment, upon administration of a composition of the invention to a plurality of fasted adult human subjects, the subjects exhibit: a mean $C_{max}$ of PPT of about 500 µg/ml to about 2000 µg/ml, about 600 µg/ml to about 1900 µg/ml, or about 700 µg/ml to about 1800 µg/ml; a mean $T_{max}$ of PPI of about 0.15 to about 2 hours, about 0.25 to about 1.75 hours, or about 0.3 hours to about 1 hour; and a mean $AUC_{(0-inf)}$ of PPI of about 1000 to about 3000 ng·hr/ml, about 1500 to about 2700 ng·hr/ml, or about 1700 to about 2500 ng·hr/ml.

Those skilled in the art will readily appreciate that numerous other embodiments, modifications and equivalents are contemplated and encompassed by the disclosure of the present invention.

All U.S. patents and published U.S. patent applications listed herein are hereby incorporated by reference in their entirety. All patents, patent applications and publications referenced herein are hereby incorporated by reference herein to the fullest extent allowed under the law.

EXAMPLES

Example 1

Enteric coated pantoprazole and an immediate release omeprazole formulation were compared in a clinical study. Thirty-two patients with nocturnal GERD symptoms were enrolled in a crossover trial; subjects were provided 40 mg of enteric coated pantoprazole (Protonix®) given at 2200 hours (bedtime) on Day 1 and prior to dinner on Days 2-6 or 40 mg of a non-enteric coated omeprazole suspension (Zegerid™) given at 2200 hours on Days 1-6. On Day 7, both PPIs were given 1 hour prior to breakfast and at 2200 hours. Continuous 24-hour gastric pH monitoring (Medtronic) was performed on Days 1, 6, and 7. Median gastric pH, percent of time gastric pH was less than 4, and the proportion of patients with "nocturnal acid breakthrough" (NAB) (>1 hr of continuous pH<4) were determined for the nighttime period (2200-0600 hours).

Nighttime median gastric pH on Day 6 is shown below. For this 8-hr period, median time that pH was >4 was greater for Zegerid™ (55%) than for Protonix® (27%) (p<0.001); median pH was 4.7 for Zegerid™ and 2.0 for Protonix® (p<0.001). Furthermore, NAB occurred in fewer Zegerid™-treated patients (17/32) than Protonix®-treated patients (25/32) (p=0.005). For the 8-hr nighttime period after twice-daily dosing, median % time that pH was >4 was greater for Zegerid™ (40 mg and 20 mg) than for Protonix® (92% vs. 37% and 79% vs. 31%, p<0.001, respectively). Median pH was also higher for Zegerid™ (40 mg and 20 mg) than for Protonix® (6.5 vs. 1.5 and 5.8 vs. 1.9, p<0.001, respectively). NAB occurred in fewer Zegerid™-treated patients than Protonix®-treated patients (2/17 vs. 12/17 and 7/15 vs. 12/15, p≤0.025, respectively). The above example is as described in Castell., Donald et al., *Zegerid Oral Suspension is More Effective than Pantoprazole (Protonix) Delayed-Release Capsules in Reducing Nighttime Gastric Acidity in GERD Patients*, American Journal of Gastroenterology, Vol 99, No. 10 S40.

Example 2

Seventeen healthy subjects were enrolled in an open-label trial. Single 20-mg doses of Zegerid™ suspension (Santarus, San Diego) were given 1 hr prior to breakfast (qAM) for 7 days. On Day 8, the 20-mg suspension was given b.i.d.: at 0830 hrs (1 hr prior to a standardized high-fat breakfast) and at 2200 hrs (bedtime). On Days 7 and 8, standardized lunch and dinner were given at 1300 and 1800 hrs. Gastric pH was continuously monitored (Medtronic) for 24 hrs following the morning doses on Days 7 and 8. The percent time pH was >4 was assessed for the 8-hr nighttime period (2200-0600 hrs) and for the 24-hr period following the morning dose. The proportion of subjects with "nocturnal acid breakthrough" (NAB) (>1 hr of continuous pH<4) was assessed for the 8-hr nighttime period.

After the bedtime dose, Zegerid™ 20 mg abruptly raised the gastric pH and sustained this effect for approximately 8 hrs. The median % time pH was >4 was greater for b.i.d dosing (87%) than for qAM dosing (39%) (p<0.001). NAB occurred in fewer subjects dosed b.i.d. (5/17 [29%]) than dosed qAM (13/17 [76%]) (p=0.005).

What is claimed is:

1. A method for treating nocturnal acid breakthrough in a subject in need thereof, the method comprising: administering to the subject a solid pharmaceutical composition comprising an inner core, an outer layer, and at least one intermediate layer, wherein;
    (a) the inner core comprises an acid labile proton pump inhibitor that is not enteric coated and is present in the composition in an amount of about 5 mg to about 60 mg and is selected from the group of omeprazole, tenatoprazole, lansoprazole, rabeprazole, esomeprazole, pantoprazole, pariprazole, leminoprazole and nepaprazole or a free base, a free acid, or a salt, ester, amide, enantiomer, isomer, or tautomer of the proton pump inhibitor;
    (b) the outer layer comprises a buffering agent that is present in the composition in an amount of about 300 mg to about 3000 mg and comprises a bicarbonate salt of a Group IA metal;
    (c) the at least one intermediate layer that exists between the inner core and the outer layer and comprises an inert and non-pH sensitive coating materials;
    (d) the administration step is performed between about 8:00 pm and about 12:00 am and at such a time so as to result in a blood serum concentration of the proton pump inhibitor of at least about 0.1 micromolar at any time point from about 12:00 am to about 6:00 am following administration; and
    (e) upon administration of the composition to a subject, the subject exhibits a Cmax of the proton pump inhibitor of about 500 µg/ml to about 2000 µg/ml; a Tmax of the proton pump inhibitor of about 0.15 to about 2 hours; and/or an AUC(0-inf) of the proton pump inhibitor of about 1000 to about 3000 ng*hr/ml.

2. The method of claim 1 wherein the administration step is performed at such a time so as to result in a blood serum concentration of the proton pump inhibitor of at least about 0.9 micromolar at any time point from about 1:00 am to about 5:00 am following administration.

3. The method of claim 1 wherein the proton pump inhibitor is omeprazole or lansoprazole.

4. The method of claim 1 wherein the proton pump inhibitor is omeprazole.

5. The method of claim 1 wherein the proton pump inhibitor is present in an amount of about 10 mg to about 40 mg on a dry weight basis.

6. The method of claim 1 wherein the buffering agent is present in an amount of about 400 mg to about 3000 mg on a dry weight basis.

7. The method of claim 1 wherein the buffering agent is present in an amount of about 500 mg to about 2500 mg on a dry weight basis.

8. The method of claim 1 wherein the composition further comprises at least one pharmaceutically acceptable excipient.

9. The method of claim 1 wherein the composition is a solid dosage form is selected from a tablet, a suspension tablet, a bite suspension tablet, a rapid dispersion tablet, a chewable tablet, an effervescent tablet, a bilayer tablet, a caplet, a capsule, a powder, a lozenge, a sachet, a cachet, a troche, a pellet, a granule and a microgranule.

10. A method for treating nocturnal acid breakthrough in a subject in need thereof, the method comprising: administering to the subject a solid pharmaceutical composition comprising an inner core, an outer layer, and at least one intermediate layer, wherein;
  (a) the inner core comprises an acid labile proton pump inhibitor that is not enteric coated and is present in the composition in an amount of about 5 mg to about 60 mg and is selected from the group of omeprazole, tenatoprazole, lansoprazole, rabeprazole, esomeprazole, pantoprazole, pariprazole, leminoprazole and nepaprazole or a free base, a free acid, or a salt, ester, amide, enantiomer, isomer, or tautomer of the proton pump inhibitor;
  (b) the outer layer comprises a buffering agent that is present in the composition in an amount of about 300 mg to about 3000 mg and comprises a bicarbonate salt of a Group IA metal;
  (c) the at least one intermediate layer that exists between the inner core and the outer layer and comprises an inert and non-pH sensitive coating materials;
  (d) the administration step is performed between about 6:00 pm and about 1:00 am and at such a time so as to result in a blood serum concentration of the proton pump inhibitor of at least about 1 micromolar at any time point from about 2:00 am to about 4:00 am following administration; and
  (e) upon administration of the composition to a subject, the subject exhibits a Cmax of the proton pump inhibitor of about 500 µg/ml to about 2000 µg/ml; a Tmax of the proton pump inhibitor of about 0.15 to about 2 hours; and/or an AUC(0-inf) of the proton pump inhibitor of about 1000 to about 3000 ng*hr/ml.

11. A method for treating nocturnal acid breakthrough in a subject in need thereof, the method comprising the steps of:
  (a) determining the subject's typical period of nocturnal acid breakthrough;
  (b) providing the subject with a pharmaceutical composition that is not enteric coated comprising:
    (i) an inner core comprising an acid labile proton pump inhibitor selected from the group of omeprazole, tenatoprazole, lansoprazole, rabeprazole, esomeprazole, pantoprazole, pariprazole, leminoprazole and nepaprazole or a free base, a free acid, or a salt, ester, amide, enantiomer, isomer, or tautomer of the proton pump inhibitor;
    (ii) an outer layer comprising a buffering agent that comprises a bicarbonate salt of a Group IA metal; and
    (iii) at least one intermediate layer that exists between the inner core and the outer layer and comprises an inert and non-pH sensitive coating materials,
      wherein pharmaceutical composition is provided at a time such that the subject exhibits a blood serum concentration of the proton pump inhibitor of at least about 0.1 micromolar at any time point during the subject's determined typical period of nocturnal acid breakthrough; and
  (c) upon administration of the composition to a subject, the subject exhibits a Cmax of the proton pump inhibitor of about 500 µg/ml to about 2000 µg/ml; a Tmax of the proton pump inhibitor of about 0.15 to about 2 hours; and/or an AUC(0-inf) of the proton pump inhibitor of about 1000 to about 3000 ng*hr/ml.

12. A method for treating nocturnal acid breakthrough in a subject in need thereof, the method comprising the steps of:
  (a) determining the subject's typical period of nocturnal acid breakthrough;
  (b) providing the subject with a pharmaceutical composition that is not enteric coated comprising:
    (i) an inner core comprising an acid labile proton pump inhibitor selected from the group of omeprazole, tenatoprazole, lansoprazole, rabeprazole, esomeprazole, pantoprazole, pariprazole, leminoprazole and nepaprazole or a free base, a free acid, or a salt, ester, amide, enantiomer, isomer, or tautomer of the proton pump inhibitor;
    (ii) an outer layer comprising a buffering agent that comprises a bicarbonate salt of a Group IA metal; and
    (iii) at least one intermediate layer that exists between the inner core and the outer layer and comprises an inert and non-pH sensitive coating materials wherein pharmaceutical composition is provided at a time such that the subject exhibits a blood serum concentration of the proton pump inhibitor of at least about 1 micromolar at any time point during the subject's determined typical period of nocturnal acid breakthrough; and
  (c) upon administration of the composition to a subject, the subject exhibits a Cmax of the proton pump inhibitor of about 500 µg/ml to about 2000 µg/ml; a Tmax of the proton pump inhibitor of about 0.15 to about 2 hours; and/or an AUC(0-inf) of the proton pump inhibitor of about 1000 to about 3000 ng*hr/ml.

* * * * *